(12) United States Patent
Takahashi et al.

(10) Patent No.: US 7,748,423 B2
(45) Date of Patent: Jul. 6, 2010

(54) COVER FILM STICKING DEVICE

(75) Inventors: Tomio Takahashi, Chikuma (JP);
Masanori Yamabe, Chikuma (JP)

(73) Assignees: Sakura Seiki Co., Ltd., Nagano (JP);
Sakura Finetek Japan Co., Ltd, Tokyo (JP)

( * ) Notice: Subject to any disclaimer, the term of this patent is extended or adjusted under 35 U.S.C. 154(b) by 580 days.

(21) Appl. No.: 11/547,470

(22) PCT Filed: Apr. 5, 2005

(86) PCT No.: PCT/JP2005/006665

§ 371 (c)(1),
(2), (4) Date: Oct. 5, 2006

(87) PCT Pub. No.: WO2005/098393

PCT Pub. Date: Oct. 20, 2005

(65) Prior Publication Data

US 2007/0151672 A1    Jul. 5, 2007

(30) Foreign Application Priority Data

Apr. 9, 2004    (JP)    ............................. 2004-116134

(51) Int. Cl.
*B32B 38/18* (2006.01)
*B26D 5/00* (2006.01)

(52) U.S. Cl. ........................ 156/350; 156/521; 156/556; 156/569; 156/578; 156/351; 156/356

(58) Field of Classification Search ................... 156/99, 156/540, 541, 542, 502, 503, 504, 506, 505, 156/57, 516, 521, 556, 569, 350, 351, 356, 156/578, 270; 422/105–116

See application file for complete search history.

(56) References Cited

U.S. PATENT DOCUMENTS

| | | | | | |
|---|---|---|---|---|---|
| 1,558,140 | A | * | 10/1925 | Zuckerman | .................. 83/312 |
| 3,715,033 | A | * | 2/1973 | Soriente | ..................... 210/193 |
| 3,974,681 | A | * | 8/1976 | Namery | ....................... 73/600 |

(Continued)

FOREIGN PATENT DOCUMENTS

GB    1 562 643 A    3/1980

(Continued)

*Primary Examiner*—Kat Wyrozebski
*Assistant Examiner*—Scott W Dodds
(74) *Attorney, Agent, or Firm*—Birch, Stewart, Kolasch & Birch, LLP

(57) ABSTRACT

The cover film sticking device is capable of securely sticking cover film pieces on specimen samples on all slide glasses stored in a basket, which starts to stick the cover film pieces formed, by cutting off long cover film unwound from a film roll to a specified length on the specimen samples on the plurality of slide glasses stored in the basket 26 taken out from a load tank 12 filled with a volatile protective solution. The sticking device is characterized by cover film length securing means for unwinding the long cover film from the film roll and extending the same until reaching cutting means so as to secure the cover film of such a length that can form the cover film pieces to be stuck onto the specimen samples on the maximum number of the slide glasses storable in the basket 26 taken out from the load tank 12.

18 Claims, 8 Drawing Sheets

U.S. PATENT DOCUMENTS

| | | | |
|---|---|---|---|
| 4,205,217 A * | 5/1980 | Araya et al. | 219/124.34 |
| 4,209,708 A * | 6/1980 | Galimberti nee Sestini | 250/548 |
| 4,268,219 A * | 5/1981 | Nakagawa et al. | 414/806 |
| 4,455,188 A * | 6/1984 | Stormby | 156/355 |
| 4,568,181 A * | 2/1986 | Nishiyama | 355/75 |
| 4,637,168 A * | 1/1987 | Kotting et al. | 451/144 |
| 5,417,922 A * | 5/1995 | Markin et al. | 422/65 |
| 5,573,626 A * | 11/1996 | Rossini et al. | 156/361 |
| 5,660,676 A * | 8/1997 | Brooks | 156/361 |
| 6,080,363 A * | 6/2000 | Takahashi et al. | 422/65 |
| 6,568,447 B1 * | 5/2003 | Sakai et al. | 156/356 |
| 2002/0154567 A1 * | 10/2002 | Husher | 366/132 |

FOREIGN PATENT DOCUMENTS

| | | |
|---|---|---|
| JP | 62-121541 U | 8/1987 |
| JP | 62-137421 U | 8/1987 |
| JP | 3-17245 Y2 | 4/1991 |
| JP | 3-55882 Y2 | 12/1991 |
| JP | 3043510 B2 | 3/2000 |
| JP | 2001-215415 A | 8/2001 |
| JP | 2003-57250 A | 2/2003 |

* cited by examiner

US 7,748,423 B2

COVER FILM STICKING DEVICE

FIELD OF TECHNOLOGY

The present invention relates to a cover film sticking device, more precisely relates to a cover film sticking device capable of sticking a cover film piece, which is formed by unwinding long cover film from a film roll and cutting off to a specified length, onto a specimen sample, which has been stuck on a slide glass and coated with a mounting medium.

BACKGROUND TECHNOLOGY

To observe a specimen of an affected part, etc., the specimen is embedded in paraffin and sliced to form into sliced pieces, each of the sliced pieces is stuck onto a slide glass and stained so as to produce a specimen sample, a mounting medium is dropped onto the specimen sample on the slide glass, and a transparent cover film piece, in which adhesive is applied to one side face, is stuck onto the specimen sample. The adhesive is molten by the mounting medium, so that the cover film piece can be stuck.

Cover film sticking devices, each of which is capable of automatically dropping a mounting medium and sticking a cover film piece, are disclosed in, for example, the following patent documents.

Patent Document 1: JP 62-121541;
Patent Document 2: JP 62-137421

One of the cover film sticking devices disclosed in Patent Documents 1 and 2 is shown in FIG. 14. In the device shown in FIG. 14, a basket 100 is turned until reaching a waiting position with keeping a plurality of slide glasses 102, 102 . . . , which are inserted and stored in the basket 100, horizontal. The slide glass 102, which is stored in a prescribed position of the basket 100 staying at the waiting position, is ejected onto a horizontal table 106 and moved on the horizontal table 106 in the ejecting direction by an ejector 104. A mounting medium is dropped onto a specimen sample on the slide glass 102, which is moved on the horizontal table 106 by the ejector 104, from a nozzle 108. The slide glass 102, on which the mounting medium has been dropped, is further moved on the horizontal table 106 by the ejector 104, and a transparent cover film 118, in which adhesive is applied to one side face, is stuck thereon. The cover film piece 118 having a specified length is formed by cutting cover film 110, which has been unwound from a film roll 112 by feeding rollers 114, with a cutter 116, and sent toward the slide glass 102 by cover rollers 120. The cover film piece 118, which has been set on the slide glass 102, is pressed onto the slide glass 102 by a sticking roller 122 so as to stick thereon. The slide glass 102, on which the cover film piece 118 has been stuck, is moved toward the basket 100 by a return ejector 124 and restored in the same position of the basket 100. Then, the basket 100 is moved upward or downward so as to stick a new cover film piece 118 onto the next slide glass 102, then the new cover film 118 is stuck onto the next slide glass 102 as well.

DISCLOSURE OF THE INVENTION

In the cover film sticking device shown in FIG. 14, the cover film pieces 118, which have been automatically cut to the specified length, can be respectively stuck onto the slide glasses 102, 102 . . . stored in the basket 100. Thus, if the basket 100, which stores the slide glasses 102, 102 . . . , is set, the cover film pieces 118 can be stuck onto specimen samples on the slide glasses 102, 102 . . . even in the night time with no operators.

The basket 100, in which the slide glasses 102, 102 . . . are stored, is usually soaked in a volatile protective solution, e.g., xylene, so as to protect the specimen sample on each slide glass 102.

Thus, when the cover film pieces 118 are stuck onto the specimen samples on the slide glasses 102, 102 . . . stored in the basket 100, the sticking work must be performed while the protective solution is left on the specimen sample on each slide glass 102.

However, if the cover film 110 wound on the film roll 112 runs out when the cover film pieces 118 are stuck onto the specimen samples on the slide glasses 102, 102 . . . stored in the basket 100, the specimen sample on the slide glass 102 is exposed in air until the new film roll 112 is set.

Especially, in the night time with no operators, if the cover film 110 wound on the film roll 112 runs out, the specimen samples on the slide glasses 102 are exposed in air for a long time, so that they will be damaged.

It is difficult to gain the same specimen samples, so the damage must be prevented so as to improve reliability of the cover film sticking device.

Therefore, an object of the present invention is to provide a cover film sticking device, which is capable of securely sticking cover film pieces onto specimen samples on all of slide glasses stored in a basket when sticking the cover film pieces, which are formed by cutting off cover film unwound from a film roll to a specified length, is started.

The inventors of the present invention thought that it is effective to secure cover film of such a length that can form cover film pieces to be stuck onto specimen samples on the maximum number of the slide glasses storable in a basket taken out from a volatile protective solution, e.g., xylene, and reached the present invention.

Namely, the cover film sticking device of the present invention comprises: a basket having a supporting section, which is formed in an inner bottom face and capable of supporting at least one point of a slide glass, the basket being capable of storing a plurality of slide glasses inserted in a direction perpendicular to the inner bottom face; a load tank storing a prescribed amount of a volatile protective solution, which is used for protecting specimen samples and in which the basket can be soaked so as to soak the specimen samples stuck on the slide glasses accommodated in the basket; conveying means for taking out the basket from the protective solution stored in the load tank and turning the basket, with keeping the slide glasses horizontal, until reaching a waiting position; transporting means for moving one of the slide glasses, which has been pulled out from a prescribed storing position of the basket staying at the waiting position to a horizontal table, to a prescribed position in the horizontal table and reinserting the slide glass into the same storing position of the basket staying at the waiting position; dropping means for dropping a mounting medium onto the specimen sample on the slide glass, which is moved on the horizontal table by the transporting means; sticking means for pressing a cover film piece, which has been formed by unwinding long cover film from a film roll and cutting off the long cover film to a specified length by cutting means, onto the specimen sample, which has been coated with the mounting medium; a basket accommodating section accommodating the basket, which is moved from the waiting position by the conveying means, when the cover film pieces are stuck onto all of the specimen samples on the slide glasses, which have been stored in the basket staying at the waiting position; and cover film length securing means for unwinding the long cover film from the film roll and extending the same until reaching cutting means so as to secure the cover film of such a length that can form the cover film pieces to be stuck onto the specimen samples on the maximum number of the slide glasses storable in the basket taken out from the load tank.

In the cover film sticking device, the cover film length securing means may include a plurality of guide rollers, which unwinds the long cover film from the film roll and extends the same until reaching the cutting means so as to secure the cover film of such the length that can form the cover film pieces to be stuck onto the specimen samples on the maximum number of the slide glasses storable in the basket taken out from the load tank; with this structure, even if the cover film wound on the film roll runs out, the specimen samples on all of the slide glasses stored in the basket can be securely covered with the cover film pieces formed from the cover film which has been extended by the guide rollers.

In the cover film sticking device, the load tank may be moved so as to insert the basket into the load tank from outside of the cover film sticking device. With this structure, the basket which may have been used in other units, e.g., a staining unit, can be automatically inserted into the load tank, so that microscopic specimen samples can be automatically produced.

The cover film sticking device may further comprise a basket sensor for detecting the basket inserted in the load tank and a conveying-control section for driving the conveying means when the basket sensor detects the basket; with this structure, the conveying means is not operated when no basket is inserted in the load tank, so that unproductive operations can be omitted.

In the cover film sticking device, a plurality of the baskets having different lengths may be inserted into the load tank, and the basket sensor may be capable of detecting the baskets having different lengths and being inserted in the load tank; with this structure, even if the baskets having different lengths are inserted in the load tank, the cover film pieces can be stuck onto the specimen samples on the slide glasses stored in the inserted baskets.

In the cover film sticking device, the basket may have a turnable hook for manually carrying, and the cover film sticking device further comprises means for turning the hook so as not to interfere with taking out the slide glass from and reinserting the same into the basket while the basket is moved to the waiting position; with this structure, the cover film pieces can be smoothly adhered onto the specimen samples on the slide glasses stored in the basket having the hook.

In the cover film sticking device, the dropping means may include a storing bottle for storing the mounting medium; a pump for feeding the mounting medium to the slide glass via a feeding tube, a bubble sensor for detecting a bubble in the feeding tube and a dropping-control section for discharging the mounting medium in the feeding tube when the bubble sensor detects a bubble in the feeding tube; with this structure, variation of amount of dropping the mounting medium, which is caused by bubbles in the feeding tube, can be prevented, so that the mounting medium can be dropped stably.

In the cover film sticking device, a filter may be attached to one end of the feeding tube, which is inserted in the storing bottle; with this structure, sucking foreign substances included in the mounting medium into the feeding tube can be prevented, and dropping the foreign substances together with the mounting medium can be prevented.

The cover film sticking device may further comprise a conveying-control section driving the conveying means, which moves the basket inserted in the load tank to the waiting position, and the dropping means may include: a storing bottle for storing the mounting medium; a pump for feeding the mounting medium to the slide glass via a feeding tube; a bubble sensor for detecting a bubble in the feeding tube; and a dropping-control section judging that the storing bottle is empty and sending a stop signal, which instructs to stop taking out the basket from the load tank, to the conveying-control section when the bubble sensor continuously detects a bubble in the feeding tube for a prescribed time, so that taking out the new basket from the load tank can be prevented when the mounting medium stored in the storing bottle runs short.

In the cover film sticking device, the sticking means may include: a feeding roller holding and unwinding the cover film from the film roll; a cutter cutting the unwound cover film so as to form the cover film piece having the specified length, the cutter acting as the cutting means; a cover roller feeding the cover film piece toward the slide glass; and a sticking roller pressing the cover film piece, which has been mounted on the slide glass, onto the slide glass, and a stick-starting point of the cover film piece, from which the cover film piece is stuck onto the slide glass, and the length of the cover film piece may be adjusted by adjusting timing of starting or stopping operation of at least one of the feeding roller and the cover roller; with this structure, even if the lengths of the slide glasses and sizes of the specimen samples are different, the sticking work can be suitable performed.

EFFECTS OF THE INVENTION

The cover film sticking device of the present invention has the cover film length securing means for unwinding the long cover film from the film roll and extending the same until reaching the cutting means so as to secure the cover film of such the length that can form the cover film pieces to be stuck onto the specimen samples on the maximum number of the slide glasses storable in the basket taken out from the load tank.

Even if the cover film wound on the film roll runs out when the sticking work for sticking the cover film piece onto the specimen sample on the slide glass stored in the basket taken out from the load tank is started, the specimen samples on the rest slide glasses can be securely covered with the cover film pieces formed from the cover film secured by the cover film length securing means.

Therefore, even if the cover film wound on the film roll runs out in the night time with no operators, the specimen samples on the slide glasses, which are left in the basket after starting the sticking work, are not exposed in air for a long time, so that damaging the specimen samples can be avoided. Therefore, reliability of the cover film sticking device can be improved.

PREFERRED EMBODIMENTS OF THE INVENTION

Figure 1:
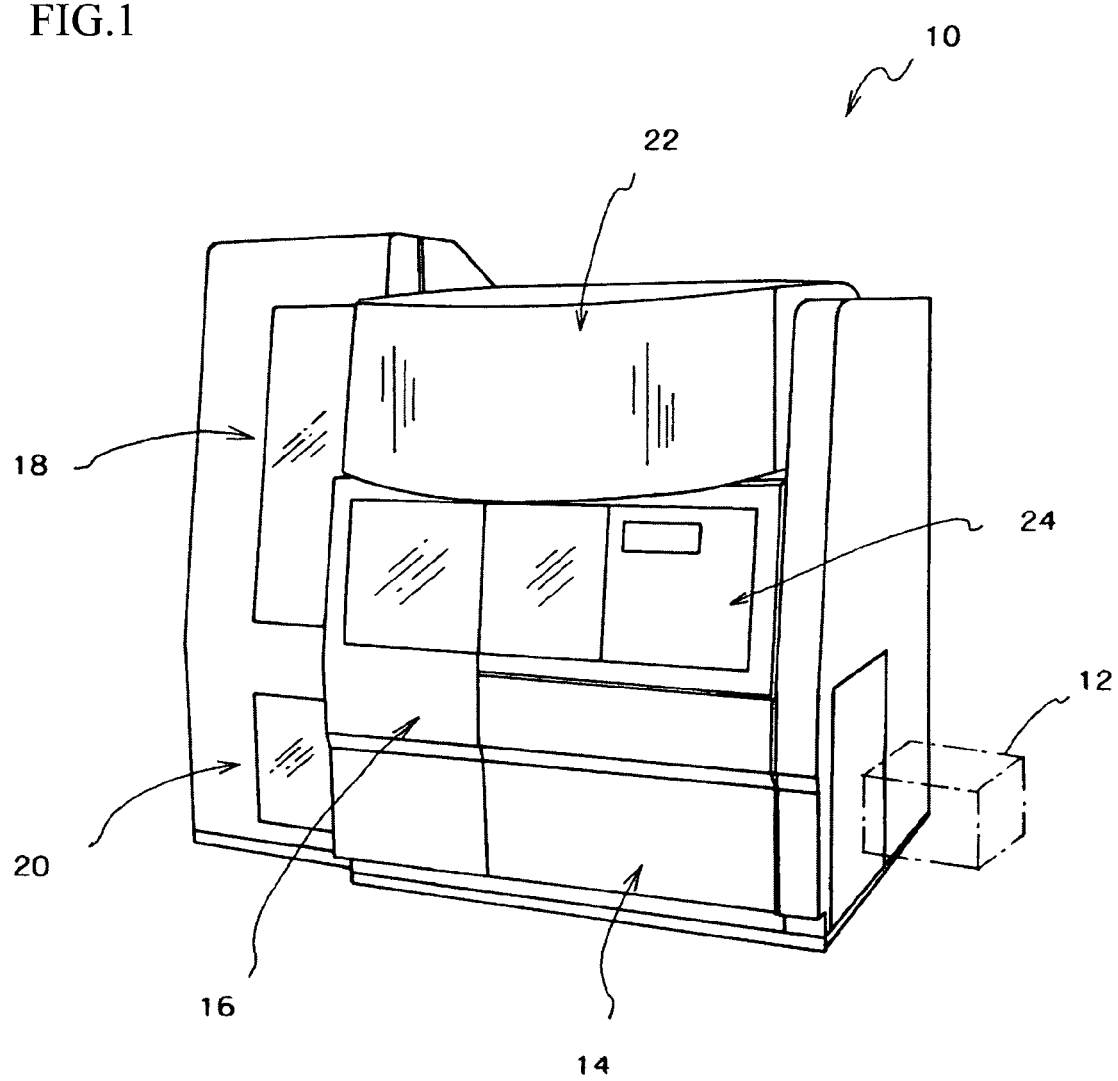
FIG. 1 is a perspective view of a cover film sticking device of the present invention.

An embodiment of the cover film sticking device of the present invention is shown in FIG. 1. FIG. 1 is a perspective view of the cover film sticking device 10, which sticks cover film, whose one side face is coated with adhesive, onto specimen samples stuck on slide glasses.

The cover film sticking device 10 comprises: a load tank setting section 14, in which a load tank 12, in which a basket storing a plurality of slide glasses, on each of which a sliced specimen sample is stuck, is inserted, is set; a main body section 16 dropping a mounting medium for melting the adhesive coating the one side face of the cover film, e.g., xylene, onto the specimen samples on the slide glasses, which are stored in the basket taken out from the load tank 12 and moved to a waiting position, and sticking cover film pieces, which have been cut to a specified length, thereon to; a cover film setting section 18, in which a film roll, on which the long cover film, which will be cut to form the cover film pieces having the specified length, is wound, is set; a bottle setting section 20, in which a storing bottle, in which the mounting medium to be dropped onto the specimen samples on the slide glasses is stored, etc. are set; and a basket accommodating section 22 accommodating the basket storing the specimen samples on the slide glasses, on each of which the cover film piece has been stuck.

Note that, the cover film sticking device 10 shown in FIG. 1 further comprises an operation panel 24, in which various function switches, etc. are provided.

Figure 2:
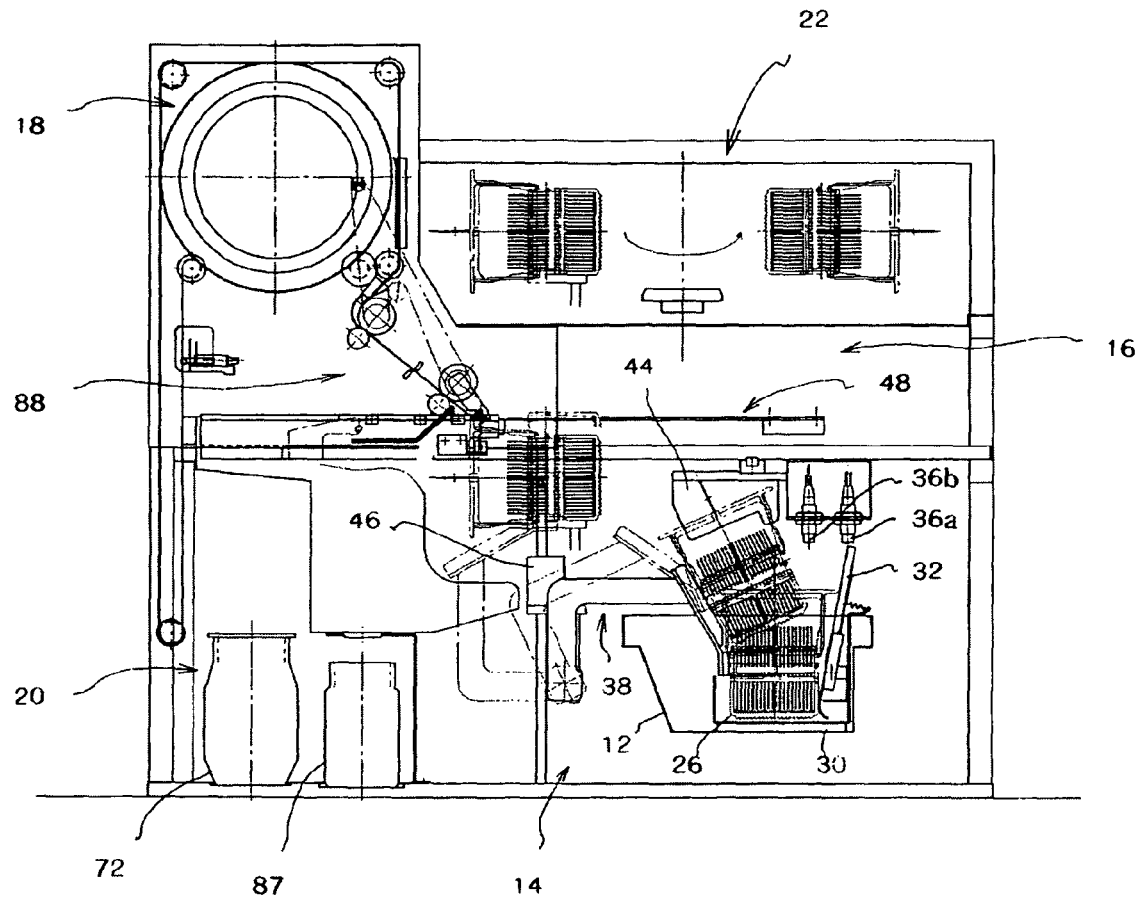
FIG. 2 is a schematic view of an inner mechanism of the cover film sticking device shown in FIG. 1.

A schematic view of an inner mechanism of the cover film setting device 10 shown in FIG. 1 is shown in FIG. 2. A volatile protective solution for protecting the specimen samples on the slide glasses, e.g., xylene, is stored in the load tank 12 set in the load tank setting section 14 shown in FIG. 2. The basket 26, in which a plurality of the slide glasses are inserted and stored, is soaked in the protective solution, and the specimen samples are also soaked in the protective solution.

The basket 26 has a supporting section, which is formed in an inner bottom face and capable of supporting at least one point of the slide glass, and the basket is capable of storing a plurality of the slide glasses inserted in a direction perpendicular to the inner bottom face. By using the basket 26, the protective solution can be suitably removed from the stored slide glasses when the basket 26 is taken out from the protective solution stored in the load tank 12.

Figure 3:
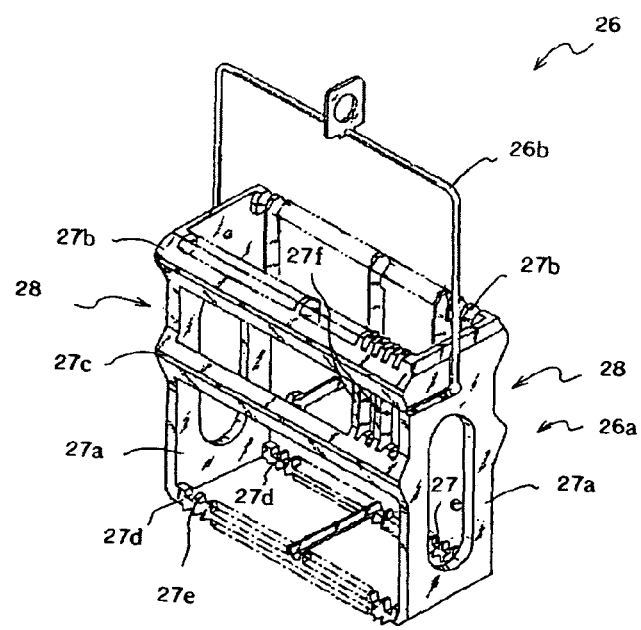
FIG. 3 is a perspective view of a basket used in the cover film sticking device shown in FIG. 1.

For example, the basket shown in FIG. 3, which is disclosed in Japanese Patent Gazette No. 7-11477, may be employed. The basket 26 shown in FIG. 3 comprises a body section 26a and a hook 26b for manually carrying, and the hook 26b is turnably attached.

The body section 26a includes: a pair of end plates 27a and 27a being arranged parallel with a prescribed separation; upper frames 27b and 27b being spanned between upper edges of the end plates 27a and 27a; intermediate frames 27c and 27c being spanned between side edges of the end plates 27a and 27a; and lower frames 27d and 27d spanned between lower edges of the end plates 27a and 27a, and a plurality of projections 27e, 27e . . . , which are arranged with a separation corresponding to a pitch of the stored slide glasses, are formed on upper edges of the lower frames 27d and 27d.

Further, guide members 27f, 27f . . . , which guide the slide glasses inserted between the projections 27e, 27e . . . , are provided to the upper frames 27b, 27b and between the upper frames 27b, 27b and the intermediate frames 27c, 27c.

Note that, in the basket 26 shown in FIG. 3, grooves 28 and 28 are formed along the upper frames 27b, 27b and the intermediate frames 27c, 27c.

Figure 4:
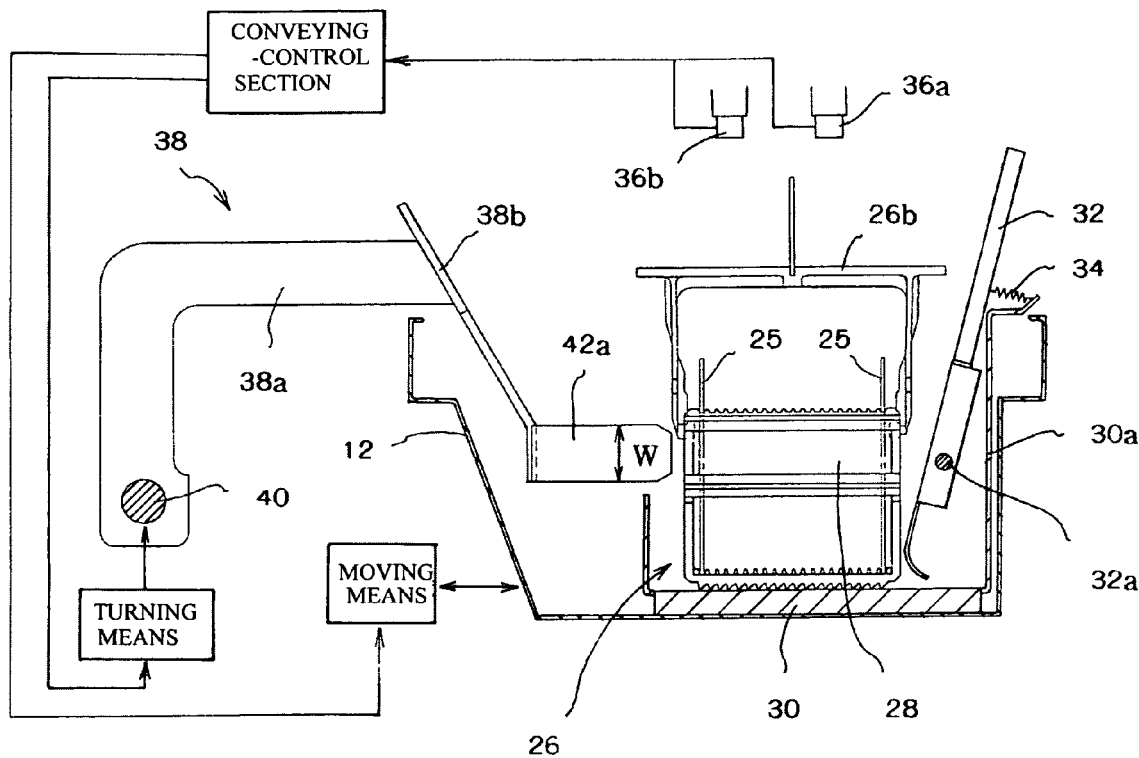
FIG. 4 is a schematic view of a load tank section 14 of the cover film sticking device shown in FIG. 1.

The load tank 12 shown in FIG. 3, in which the basket 26 is inserted, is moved inside and outside of the cover film sticking device 10, as shown in FIG. 4, by proper means, e.g., motor, cylinder unit.

In the load tank 12, a mounting section 30, on which the basket 26 inserted in the load tank 12 is mounted, is fixed near a surface of one of side walls of the load tank 12 as shown in FIG. 4, and a rectangular member 32, which is capable of turning about a rotary shaft 32a located at a mid part thereof, is provided near a wall section 30a of the mounting section 30.

A spring 34, which acts as a biasing member for biasing one end of the rectangular member 32 toward the wall section 30a, is provided between an upper end of the wall section 30a and the one end of the rectangular member 34, and the other end of the rectangular member 32 is turned and moved away from the wall section 30a or moved toward the basket 26 mounted on the mounting section 30 and contacts the basket 26.

A size of the basket 26 depends on number of the slide glasses stored therein. Therefore, sensors 36a and 36b, which detect the one end of the rectangular member 32, are arranged in a moving direction of the load tank 12 with a prescribed separation. The sensor 36b is located on the inner side of the cover film sticking device 10 with respect to the sensor 36a.

Figure 5:
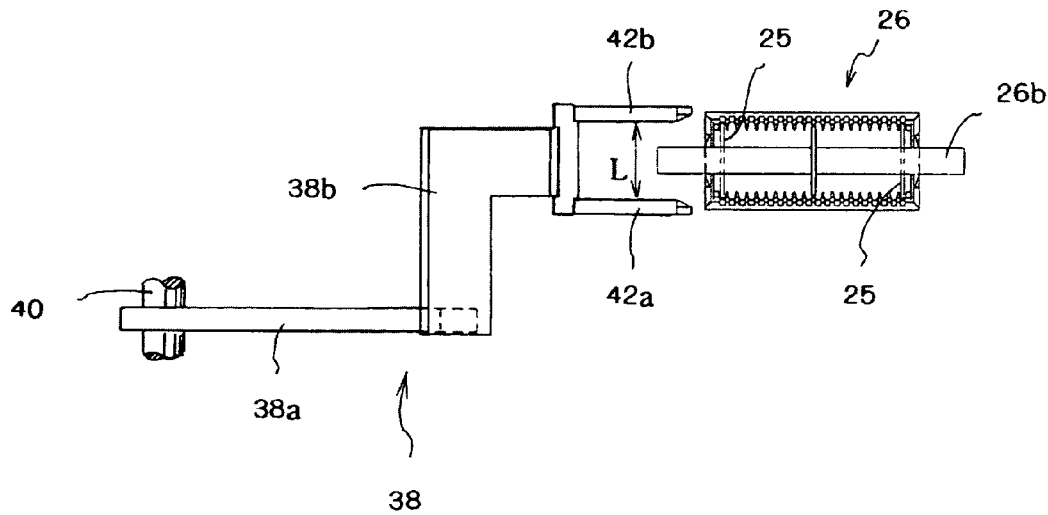
FIG. 5 is an explanation view explaining relationship between a basket 26 inserted in the load tank 12 and U-shaped claw sections 42a and 42b provided to a front end of an arm 38.

As shown in FIGS. 4 and 5, a rotary arm 38, which has L-shaped sections 38a and 38b and which is turned about a rotary shaft 40 provided to a rear end as shown in FIG. 2, is provided near the load tank 12. A U-shaped claw sections 42a and 42b are provided to a front end of the arm 38. As shown in FIG. 5, a clearance L, in which the basket 26 will be inserted, is formed between the claw sections 42a and 42b, and the claw sections 42a and 42b having a width W can be inserted into the grooves 28a and 28 of the basket 26 as shown in FIG. 4.

Means for turning the arm 38 and means for moving the load tank 12, e.g., motors, are controlled by a conveying-control section, which receives signals from the sensors 36a and 36b.

In the load tank setting section 14 shown in FIGS. 4 and 5, the arm 38 is turned as shown in FIG. 4 for inserting the claw sections 42a and 42b in the grooves 28 and 28 of the basket 26 after the basket 26 is mounted on the mounting section 30 of the load tank 12.

Next, the load tank 12 is moved toward the claw sections 42a and 42b by the moving means so as to insert the basket 26 in the clearance between the claw sections 42a and 42b, and then only the motion of the basket 26 is stopped.

By stopping the motion of the basket 26, which is moved with the motion of the load tank 12, by the claw sections 42a and 42b of the arm 38, the basket 26 presses the other end of the rectangular member 32, which is moved together with the load tank 12, in the opposite direction of the biasing direction of the spring 34. With this action, the rectangular member 32 is turned against elasticity of the spring 34, and the one end of the rectangular member 32 is moved close to the sensor 36a so that the sensor 36a sends the detecting signal to the conveying-control section.

Upon receiving the signal from the sensor 36a, the conveying-control section judges that the size of the detected basket 26 is larger than that of the basket 26 to be detected by the sensor 36b, and the conveying-control section controls following actions.

Note that, if no sensors 36a and 36b detect the one end of the rectangular member 32, the conveying-control section judges that no basket 26 is inserted in the load tank 12 and stops the following actions.

Figure 6:
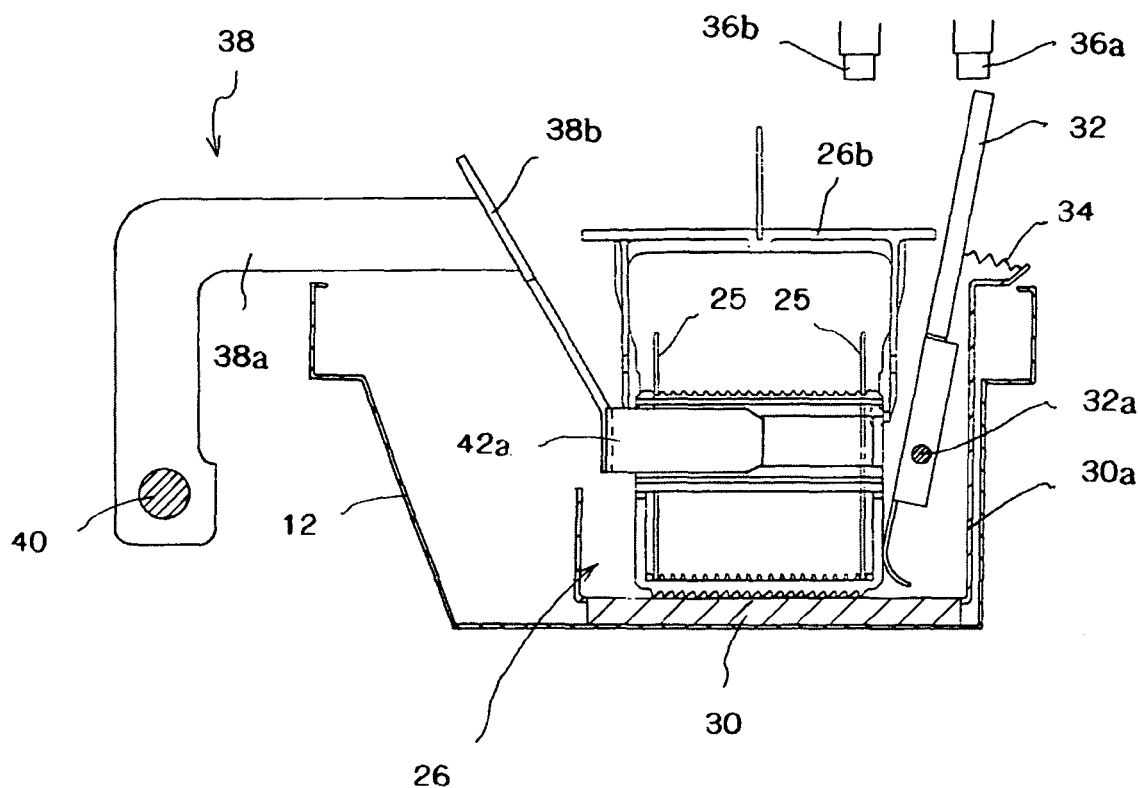
FIG. 6 is an explanation view of a state in which the load tank 12 is moved and the basket 26 is inserted in the claw sections 42a and 42b.

When the claw sections 42a and 42b are inserted in the grooves 28 and 28 of the basket 26, which has been mounted on the mounting section 30 of the load tank 12 and which has the turnable hook 26b for manually carrying, and the one end of the rectangular member 32 is detected as shown in FIG. 6, the conveying-control section sends a signal for driving the turning means so as to start to turn the arm 38 as shown in FIG. 2.

By turning the arm 38, the basket 26 held by the claw sections 42a and 42b is taken out from the load tank 12 and turned until the stored slide glasses 25, 25 . . . are horizontalized.

While the turning action, the turn is once stopped, and a hook pusher 44 is moved in a direction perpendicular to the surface of the drawing of FIG. 2 so as to turn down the hook 26b of the basket 26. By turning down the hook 26b, the slide glasses 25, 25 . . . stored in the basket 26 are not interfered with the hook 26b when they are taken out and restored.

The basket 26, whose hook 26b has been turned down, is turned until the stored slide glasses 25, 25 . . . are horizontalized, mounted on an elevating table 46, which is vertically moved, and moved upward until reaching a waiting position.

Figure 7:
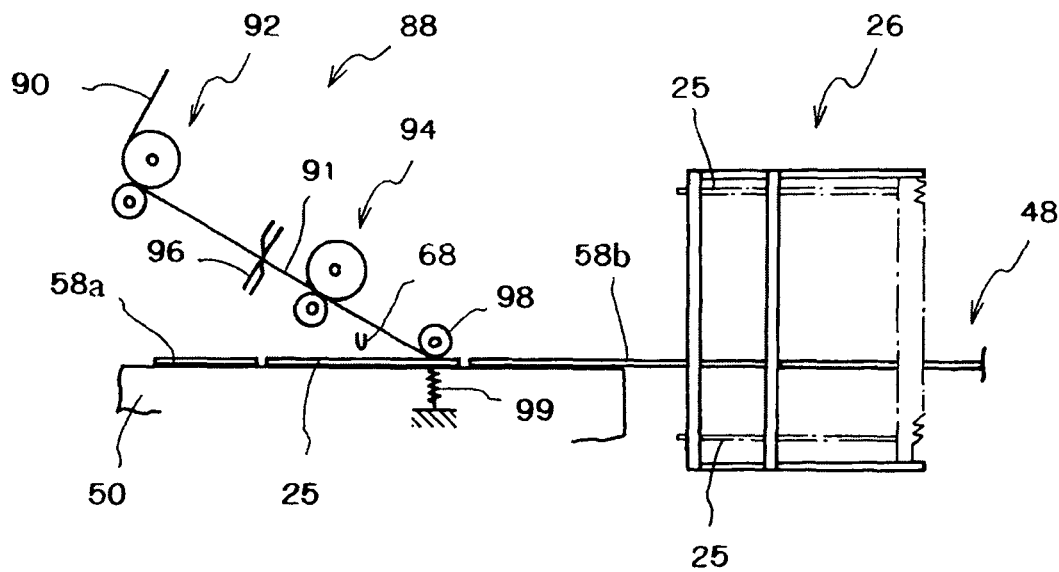
FIG. 7 is a schematic view of a main body section 16 of the cover film sticking device shown in FIG. 1.

Each of the slide glasses 25, 25 . . . , which are stored in the basket 26 located at the waiting position, is taken out and moved to a horizontal table 50, as shown in FIG. 7, by transporting means 48, which is provided to the main body section 16 of the cover film sticking device 10. The slide glass 25 on the horizontal table 50 is moved to a prescribed position in the horizontal table 50 by the transporting means 48 and restored in the same place of the basket 26 located at the waiting position from the prescribed position.

Figure 8:
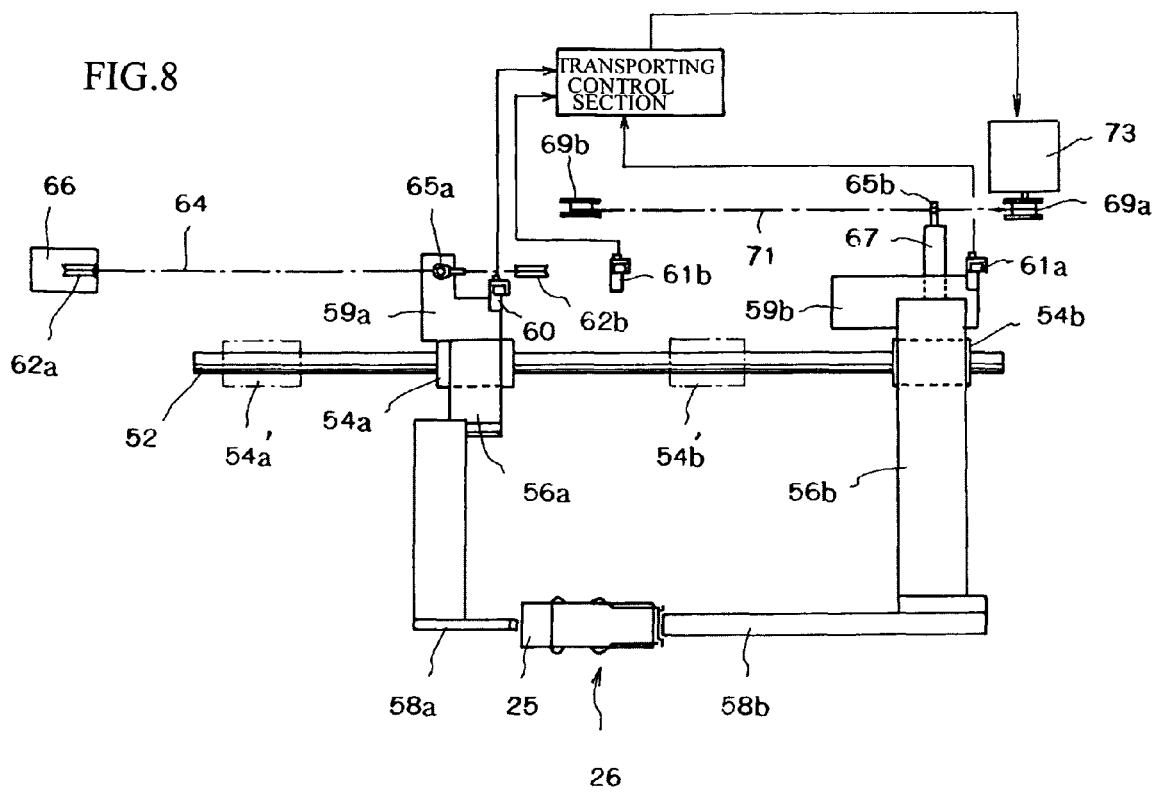
FIG. 8 is a schematic view of transporting means, which is attached to the main body section 16 and capable of transporting the slide glasses stored in the basket 26.

The transporting means 48 is shown in FIG. 8. In the transporting means shown in FIG. 8, one ends of plate members 56a and 56b are respectively fixed to sliders 54a and 54b, which are slidably provided to a guide member 52, and detection plates 59a and 59b are respectively provided to the one ends. An ejector 58b, which pushes the slide glass 25 stored in the basket until reaching the prescribed position in the horizontal table 50, and a return ejector 58a, which pushes the slide glass 25, which has been moved to the prescribed position by the ejector 58b, to return to the same place of the basket 26, are respectively provided to the other ends of the plate members 56a and 56b.

A belt 71, which is engaged with pulleys 69a and 69b, is fixed to a member 67, which is extended from the plate member 56b, by a fixing member 65b, and the pulley 69a is driven by a motor 73, which is rotated in a normal direction and a reverse direction by control means. Therefore, the plate member 56b is moved along the guide member 52 by the motor 73, and the ejector 58b is also moved along the guide member 52.

On the other hand, the plate member 56a is moved by a wire 64, which is engaged with pulleys 62a and 62b and fixed to the detection plate 59a provided to the one end of the plate member 56a by a fixing member 65a, and a balancer 66, which is suspended from an end of the wire 64 on the pulley 62a side.

Figure 9:
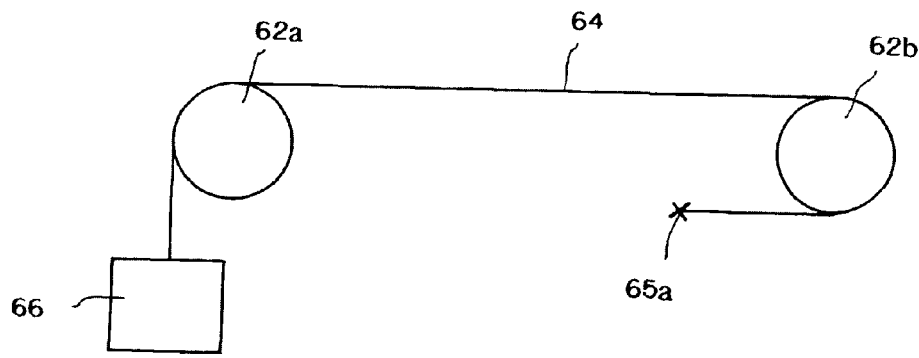
FIG. 9 is an explanation view of a balancer 66 attached to the transporting means.

As shown in FIG. 9, the balancer 66 is suspended from the end of the wire 64, which is engaged with the pulleys 62a and 62b, on the pulley 62a side, and the other end of the wire on the pulley 62b side is fixed to the fixing member 65a of the detection plate 59a. With this structure, a force for moving toward the pulley 62b is applied to the plate member 56a and the return ejector 58a.

Figure 10:
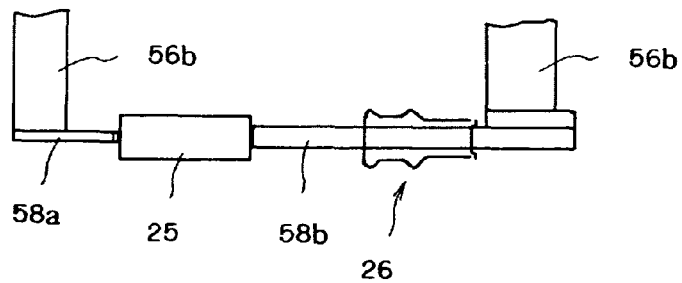
FIG. 10 is an explanation view of a state in which the slide glass 25 stored in the basket 26 is taken out by the transporting means.

Therefore, as shown in FIG. 10, the slide glass 25 stored in the basket located at the waiting position is sandwiched between the ejectors 58a and 58b and moved to the prescribed direction on the horizontal table 50.

Since the slide glass 25 sandwiched between the ejectors 58a and 58b is moved, a preferable weight of the balancer 66 is designed to prevent the slide glass 25 from damage even if the movement of the slide glass is locked in the mid way.

Sensor 60, which detects the detection plate 59a when a front end of the return ejector 58a reaches a position close to the basket 26 located at the waiting position, is provided to the detection plates 59a of the plate member 56a shown in FIG. 8.

Further, a right sensor 61a and a left sensor 61b for detecting the detection plate 59b are provided, and the right sensor 61a is located at a specified position so as to detect the detection plate 59b when a front end of the ejector 58b reaches a position close to the basket 26 located at the waiting position, as shown in FIG. 8. On the other hand, the left sensor 61b is located at another specified position so as to detect the detection plate 59b when the sliders 54a and 54b reach positions 54a' and 54b' shown in FIG. 8. When the left sensor 61b detects the detection plate 59b, the ejector 26 passes through the basket 26 and extended until the prescribed position in the horizontal table 50 as shown in FIG. 10.

Detection signals of the sensors 60, 61a and 61b are sent to a transporting-control section, and signals for driving and stopping the motor 73 are transmitted from the transporting-control section.

When the slide glass 25 stored in the basket 26 located at the waiting position is taken out and mounted on the horizontal table 50, the motor 73 is driven by the signal sent from the transporting-control section and rotated in the normal direction, so that a front end of the ejector 58b contacts one end of the slide glass 25 stored in the basket 26 and pushes out the slide glass 25 from the basket 26 toward the horizontal table 50.

The slide glass 25 pushed out from the basket 26 by the ejector 58b is moved away from the basket 26, by the ejector 58b, against a force of the balancer 66, which is applied when the other end of the slide glass contacts a front end of the return ejector 58a. At that time, the plate member is moved toward the left sensor 61b, the detection signal sent from the right sensor 61a, which has detected the plate member 59b, to the transporting-control section is turned off, the detection plate 59a of the plate member 56a is also moved, and the detection signal sent from the sensor 60, which has detected the plate member 59a, to the transporting-control section is also turned off.

Next, when the detection plate 59b of the plate member 56b is moved and detected by the left sensor 61b, the slide glass 25, which has been transported by the ejector 58b, is located at the prescribed position in the horizontal table 50 as shown in FIG. 10. The transporting-control section, which has received the detection signal of detecting the detection plate 59 sent from the left sensor 61b, transmits a signal for stopping the motor 73 and the signal for rotating the motor in the reverse direction.

Therefore, the front end of the ejector 58b contacts and moves the slide glass 25, which is pushed by the return ejector 58a, toward the basket 26.

The ejector 58b passes through the basket 26 and restores the slide glass 25 in the initial place of the basket 26, and then the transporting-control section, which receives the detection signal of detecting the detection plate 59b sent from the right sensor 61a, transmits the signal for stopping the reverse rotation of the motor 73.

In case of storing no slide glass 25 in the prescribed place in the basket 26 located at the waiting position, even if the detection plate 59b of the plate member 56b is detected by the right sensor 61b, the detection plate 59a of the plate member 56a is not detected by the right sensor 60. Therefore, even if the detection signal sent from the right sensor 61a is turned off, the conveying-control section judges that no slide glass 25 is stored in the prescribed place in the basket 26, and the conveying-control section tries to convey the next slide glass 25 when the detection signal sent from the sensor 60 is turned on.

The slide glass 25, which has been moved to the horizontal table 50 from the prescribed position of the basket 26, is further moved to a prescribed place in the horizontal table 50, and the mounting medium is dropped onto the specimen sample on the slide glass 25 from a nozzle 68 as shown in FIG. 7 and the cover film piece is stuck thereon while the slide glass is located at the prescribed position and moved to the basket 26 located at the waiting position so as to restore in the same place.

Figure 11:
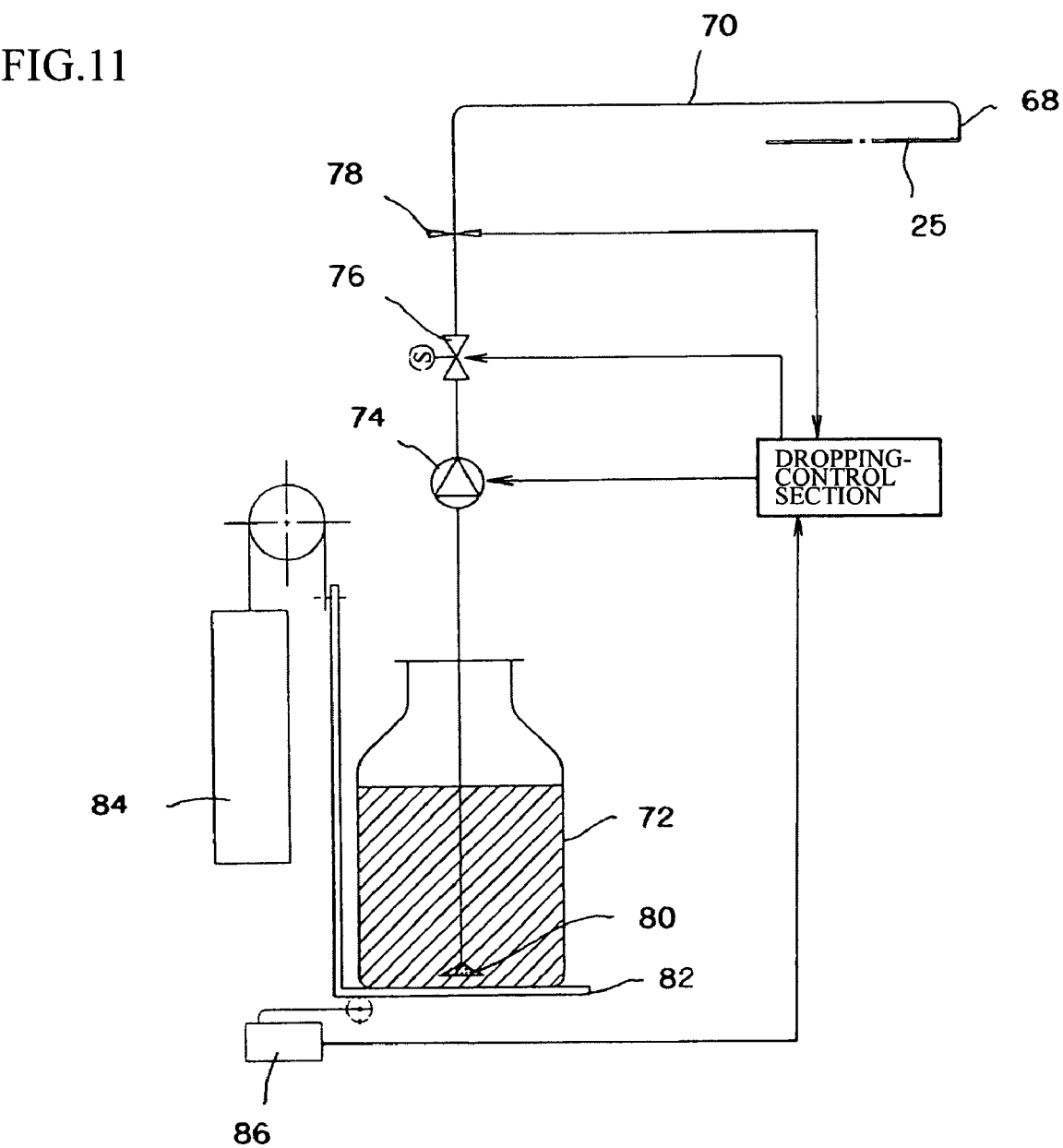
FIG. 11 is a schematic view of dropping means for dropping a mounting medium onto the slide glass 25 transported by the transporting means.

Means for dropping the mounting medium shown in FIG. 11 is connected to the metallic nozzle 68. The dropping means includes a transparent feeding tube 70, which feeds the mounting medium stored in a storing bottle 72 set in the bottle setting section 20 of the cover film sticking device 10 shown in FIG. 1, and a pump 74, an electromagnetic valve 76 and a bubble sensor 78 are provided to the feeding tube 70 in that order from the storing bottle 72 side.

The pump 74 and the valve 76 are controlled by a dropping-control section, and the bubble sensor 78 sends a bubble detection signal to the dropping-control section when the bubble sensor detects a bubble or bubbles in the feeding tube 70.

A filter 80 is attached to a front end of the feeding tube 70, which is inserted in the storing bottle 72, so as not to suck dusts, etc., which have been in the storing bottle 72, into the feeding tube 70 when the storing bottle 72 is exchanged.

The storing bottle 72 is mounted on a table 82, to which an upward force is applied by a weight 84 whose weight is equal to the sum of a weight of a tare of the storing bottle 72 and a weight of the mounting medium stored in the storing bottle 72. Since the table 82 is moved upward and downward by the amount of the mounting medium stored in the storing bottle 72, the amount of the mounting medium stored in the storing bottle 72 can be know by measuring the position of the table 82. Thus, a sensor 86 sends a detection signal to the dropping-control section when the amount of the mounting medium in the storing bottle 72 is less than a prescribed amount and the table 82 is upwardly moved until reaching a prescribed position. Upon receiving the detection signal sent from the sensor 86, the dropping-control section sends a stop signal, which indicates to stop taking out the next basket 26 from the load tank 12, to the conveying-control section (see FIG. 4).

In some cases, air is sucked into the feeding tube 70, and a bubble or bubbles are formed in the feeding tube 70. The bubble in the feeding tube 70 varies the amount of the mounting medium dropped onto the slide glass 25. Upon receiving the detection signal sent from the bubble sensor 78, the dropping-control section actuates the pump 74 so as to discharge all of the mounting medium in the feeding tube 70 from the nozzle 68 and transmits a signal for opening the electromagnetic valve 76. The mounting medium discharged from the nozzle 68 is collected in a drain bottle 87. When the mounting medium in the feeding tube 70 is completely discharged, the dropping-control section stops the pump 74 and transmits a signal for closing the electromagnetic valve 76.

In the dropping means shown in FIG. 11, a suitable distance between the bubble sensor 78 and the nozzle 68 is designed to securely feed the mounting medium onto the maximum number of the slide glasses 25 storable in the basket 26 located at the waiting position. By securing the prescribed amount of the mounting medium capable of feeding the mounting medium onto the maximum number of the slide glasses 25 storable in the basket 26 located at the waiting position, an undesirable case, in which the mounting medium cannot be dropped onto a part of the slide glasses 25 stored in the basket 26 located at the waiting position, can be avoided.

In the dropping means shown in FIG. 11, the amount of the mounting medium stored in the storing bottle 72 is measured by the weight 64, the table 84 and the sensor 86, but the dropping-control section may judge that the storing bottle 72 is empty and send a stop signal, which instructs to stop taking out the basket 26 from the load tank 12, to the conveying-control section (see FIG. 4) when the dropping-control section continuously receives the bubble detection signals sent from the bubble sensor 78 for a prescribed time instead of the weight 64, the table 84 and the sensor 86.

Note that, the empty of the storing bottle 72 may be indicated, and the pump 74 may be stopped and the electromagnetic valve 76 may be closed simultaneously.

The cover film piece is pressed and stuck onto the slide glass 25, on which the mounting medium has been dropped by the dropping means shown in FIG. 11, by the sticking means shown in FIG. 7.

Figure 12:
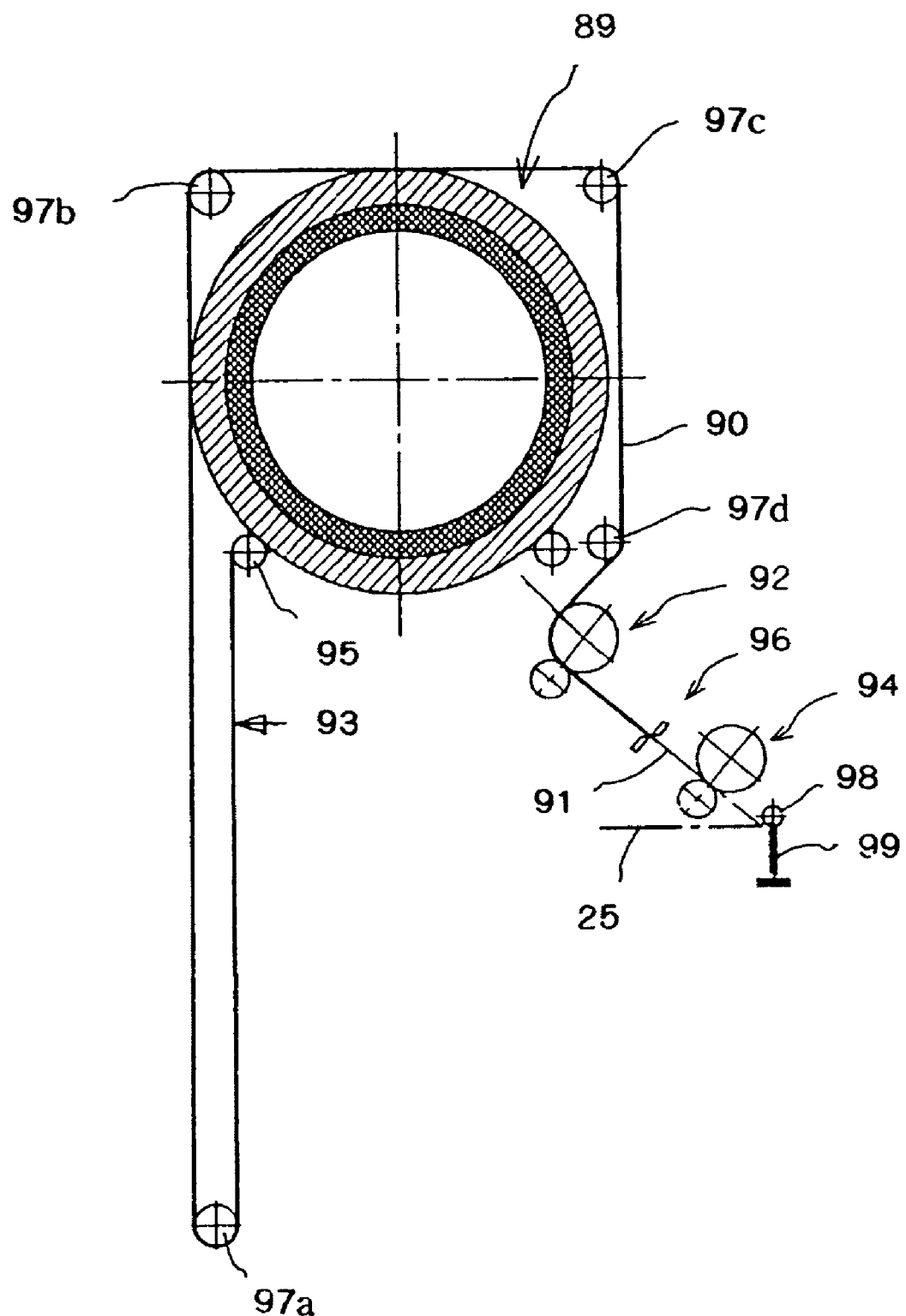
FIG. 12 is a schematic view of an example of a cover film setting section 18 of the cover film sticking device shown in FIG. 1.

As shown in FIG. 7, the sticking means feeds long cover film 90 to the slide glass 25 by a pair of feeding rollers 92 and a pair of cover rollers 94, and the cover film 90 is cut by a cutter 96 provided between the feeding rollers 92 and the cover rollers 94 so as to form the cover film piece 91 having the specified length as shown in FIG. 12. The cover film piece 91 is pressed and stuck onto the slide glass 25 by a sticking roller 98. A rotary shaft of the sticking roller 98 is biased toward the horizontal table 50 by a prescribed force of a spring 99, which acts as a biasing member, so that the cover film pieces 91 can be stuck onto the slide glasses 25 with a fixed force.

In the sticking means shown in FIGS. 7 and 12, the cutter 96, which acts as cutting means, cuts the cover film 90, which is fed the specified length at constant timing from the start of the feed by the feeding rollers 92, so as to form the cover film pieces 91 having the specified length set by the operation panel 24 (see FIG. 1). Therefore, the length of the cover film pieces 91 can be made shorter by actuating the cutter 96 at the rapid timing from the start of the feed by the feeding rollers 92.

A stick-starting point of the cover film piece 91, from which the cover film piece is stuck onto the slide glass 25, can be adjusted by adjusting timing of starting the cover rollers 94. By starting the cover rollers earlier with respect to the slide glass 25 moved on the horizontal table 50, the cover film piece 91 can be stuck at a position close to the one end of the slide glass 25. The stick-starting point of the cover film piece 91 with respect to the end of the slide glass 25 may be set by the operation panel 24, so that the cover film piece 91 can be stuck at a prescribed position.

In the sticking means shown in FIG. 7, the slide glass 25, which has been stored in the prescribed place of the basket 26 located at the waiting position, is sandwiched between the ejectors 58a and 58b and moved onto the horizontal table 50 by the ejector 58b, the slide glass 25 is further moved away from the basket 26 by the ejector 58b, and the transportation of the slide glass 25 by the ejector 58b is stopped after passing the nozzle 68.

Next, the slide glass 25 is moved toward the basket 26 by the return ejector 58a, the mounting medium is dropped from the nozzle 68 when the nozzle 68 is relatively located at a prescribe position with respect to the one end of the slide glass 25, then the feeding rollers 92 and the cover rollers 94 are driven and the cutter 96 is actuated at the prescribed timing, so that the front end part of the cover film 90 having the specified length is fed to the prescribed position of the slide glass 25. The cover film piece 91, which has been fed to the prescribed position of the slide glass 25, pressed by the sticking roller 98 and stuck onto the slide glass 25.

When the slide glass 25 is moved toward the basket 26 by the return ejector 58a, a moving speed of the slide glass 25 can be adjusted by adjusting a reverse rotational speed of the motor 73, which drives the return ejector 58b contacting the slide glass 25.

The long cover film 90 shown in FIG. 7 is fed by cover film feeding means of the cover film setting section 18 shown in FIG. 1.

In the cover film feeding means, as shown in FIG. 12, the cover film 90 is unwound from a film roll 89, on which the cover film 90 is wound, extended by an extending roller 95, further extended via a sensor 93 for detecting a rear end of the cover film 90 and guide rollers 97a-97d, and fed to the pair of feeding rollers 92. The length of the cover film 90 between the sensor 93 and the feeding roller 92 is designed as a length which can form the cover film pieces 91 to be stuck onto the specimen samples on the maximum number of the slide glasses 25 storable in the basket 26 located at the waiting position. By employing cover film length securing means including the guide rollers 97a-97d provided around the film roll 89, the cover film pieces 91 can be stuck onto all of the slide glasses 25 stored in the basket 26 located at the waiting position even if the sensor 93 detects the rear end of the cover film 90 while the slide glasses 25 stored in the basket 26 located at the waiting position are processed.

Note that, a detection signal of the sensor 93 is sent to the conveying-control section (see FIG. 4), so that the next basket 26 is not taken out from the load tank 12.

The slide glass 25, on which the cover film piece 91 has been stuck, is restored in the initial place of the basket 26 located at the waiting position. Upon sticking the cover film pieces 91 onto all of the slide glasses 25 stored in the basket 26 located at the waiting position, the basket 26 is accommodated in the basket accommodating section 22 (see FIG. 1), which is located above the waiting position, by the elevating table 46. A basket accommodating member is rotatably provided in the basket accommodating section 22 so as to accommodate a plurality of the baskets 26.

Figure 13:
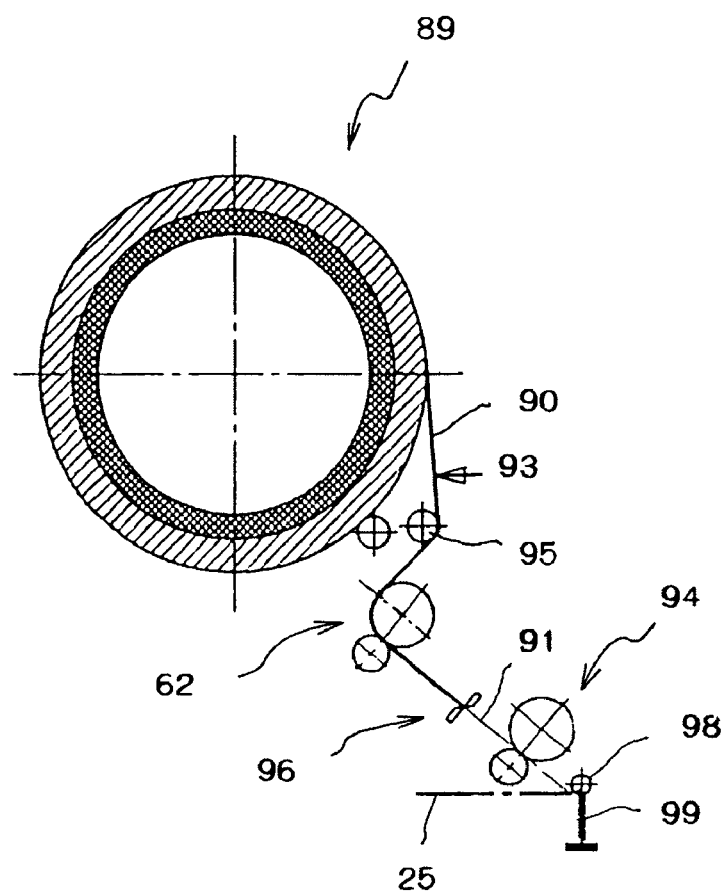
FIG. 13 is a schematic view of another example of the cover film setting section 18.
Figure 14:
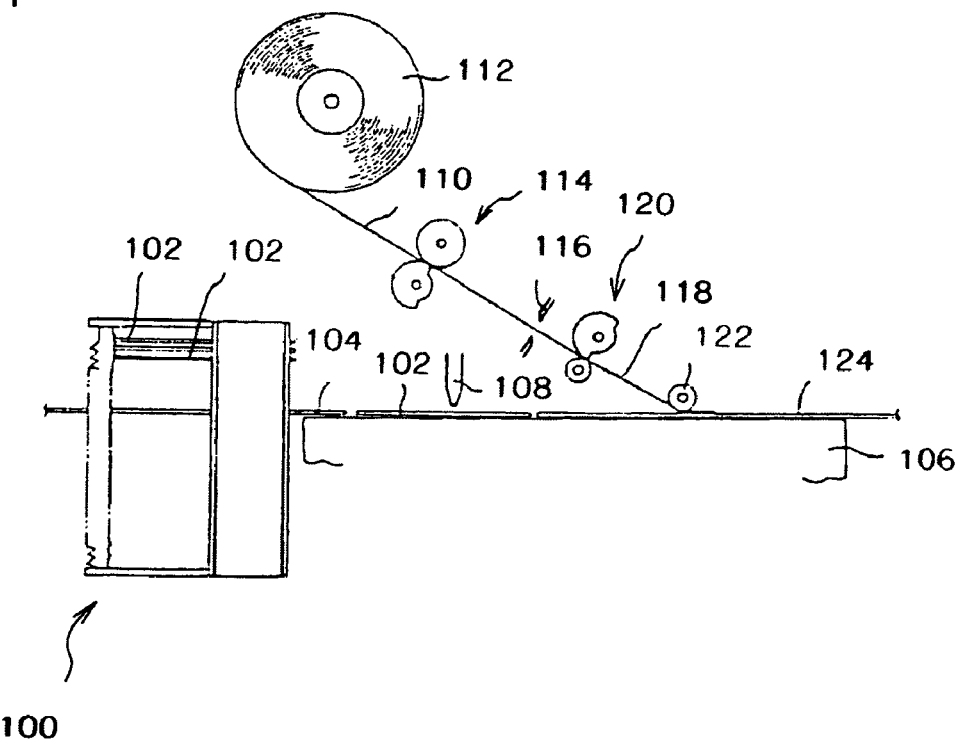
FIG. 14 is a schematic view of the conventional cover film sticking device.

The cover film length securing means shown in FIG. 12 secures the length of the cover film 90 by extending the cover film 90 with the guide rollers 97a-97d provided around the film roll 89, so a sufficient space is required in the cover film sticking device 10. A mark may be previously put at a position of the cover film 90, which is separated the prescribed length from the rear end, namely the prescribed length can form the cover film pieces 91 to be stuck onto the specimen samples on the maximum number of the slide glasses 25 storable in the basket 26 located at the waiting position, and the mark may be detected by the sensor 93, which is provided immediately before the feeding rollers 92, as shown in FIG. 13.

Further, as shown in FIG. 1, the load tank 12 can be outwardly drawn from the cover film sticking device 10, so the basket 26, in which the slide glasses 25 on which specimen samples stained by a staining unit, can be automatically inserted therein. Therefore, microscopic specimen samples can be automatically produced by connecting the cover film sticking device 10 with other units or devices, e.g., staining unit.

The load tank 12 may accommodate a plurality of baskets 26, 26 . . . in parallel. In this case, a plurality of the rectangular members 32 must be arranged parallel.

In the above described description, the adhesive is applied to one side face of the cover film 90 or the cover film piece 91, but the present invention can be applied to a cover film sticking device, in which cover film or cover film pieces having no adhesive faces are used. In this case, the mounting medium capable of adhering the cover film to a slide glass must be used.

The invention claimed is:

1. A cover film sticking device, comprising:
a basket having a supporting section, which is formed in an inner bottom face and capable of supporting at least one point of a slide glass the basket being capable of storing a plurality of slide glasses inserted in a direction perpendicular to the inner bottom face;
a load tank storing a prescribed amount of a volatile protective solution, which is used for protecting specimen samples and in which the basket can be soaked so as to soak the specimen samples stuck on the slide glasses accommodated in the basket;
a conveyor for taking out the basket from the protective solution stored in the load tank and turning the basket, with keeping the slide glasses horizontal, until reaching a waiting position;
a transporter for moving one of the slide glasses, which has been pulled out from a prescribed storing position of the basket staying at the waiting position to a horizontal table, to a prescribed position in the horizontal table and reinserting the slide glass into the same storing position of the basket staying at the waiting position;
a dropping device for dropping a mounting medium onto the specimen sample on the slide glass, which is moved on the horizontal table by the transporter;
a cover film length securing device for unwinding the long cover film from the film roll and extending the long cover film until reaching a cutting device so as to ensure that the cover film has a length that is able to form a sufficient number of cover film pieces having a specified length which is needed to stick onto the specimen samples on a maximum number of the slide glasses storable in the basket taken out from the load tank,
a sticking device for respectively pressing each of the cover film pieces onto the specimen, each of which has been previously coated with the mounting medium;
wherein when the cover film pieces are stuck onto all of the specimen samples on the slide glasses which have been stored in the basket staying at the waiting position, the cover film sticking device being adapted to move the basket from the waiting position to a basket accommodating section by the conveyer;

the cover film sticking device further comprising an end-of-roll detecting sensor and signaling device for detecting a rear end of the long cover film and for emitting a signal to stop a subsequent basket from being taken out of the load tank when the rear end of the long cover film is detected.

2. The cover film sticking device according to claim 1, wherein the cover film length securing device which includes a plurality of guide rollers, unwinds and extends the long cover film from the film roll until reaching the cutting device so as to secure the cover film to such a length that can form the cover film pieces to be stuck onto the specimen samples on the maximum number of the slide glasses storable in the basket taken out from the load tank.

3. The cover film sticking device according to claim 1, wherein the load tank can be moved so as to insert the basket into the load tank from outside of the cover film sticking device.

4. The cover film sticking device according to claim 1, further comprising:
a basket sensor for detecting the basket inserted in the load tank; and
a conveying-control section driving said conveyor when the basket sensor detects the basket.

5. The cover film sticking device according to claim 4, wherein a plurality of the baskets having different lengths can be inserted into the load tank, and the basket sensor is capable of detecting the baskets having different lengths and being inserted in the load tank.

6. The cover film sticking device according to claim 4, wherein the basket has a turnable hook for manually carrying the basket, and the cover film sticking device further comprises a turning device for turning the hook so as not to interfere with taking out the slide glass from and reinserting slide glass into the basket while the basket is moved to the waiting position.

7. The cover film sticking device according to claim 1, wherein the dropping device includes:
a storing bottle for storing the mounting medium;
a pump for feeding the mounting medium to the slide glass via a feeding tube;
a bubble sensor for detecting a bubble in the feeding tube; and
a dropping-control section discharging the mounting medium in the feeding tube when the bubble sensor detects a bubble in the feeding tube.

8. The cover film sticking device according to claim 7, wherein a filter is attached to one end of the feeding tube, which is inserted in the storing bottle.

9. The cover film sticking device according to claim 1, further comprising a conveying-control section driving the conveyor, which moves the basket inserted in the load tank to the waiting position, and
wherein the dropping device includes:
a storing bottle for storing the mounting medium;
a pump for feeding the mounting medium to the slide glass via a feeding tube;
a bubble sensor for detecting a bubble in the feeding tube; and
a dropping-control section judging that the storing bottle is empty and sending a stop signal, which instructs to stop taking out the basket from the load tank, to the conveying-control section when the bubble sensor continuously detects a bubble in the feeding tube for a prescribed time.

10. The cover film sticking device according to claim 9, wherein a filter is attached to one end of the feeding tube, which is inserted in the storing bottle.

11. The cover film sticking device according to claim 1, wherein the sticking device includes:
a feeding roller holding and unwinding the cover film from the film roll;
a cutter cutting the unwound cover film so as to form the cover film piece having the specified length, the cutter acting as the cutting device;
a cover roller feeding the cover film piece toward the slide glass;
a sticking roller pressing the cover film piece, which has been mounted on the slide glass, onto the slide glass, and
a stick-starting point of the cover film piece, from which the cover film piece is stuck onto the slide glass, and the length of the cover film piece is adjusted by adjusting timing of starting or stopping operation of at least one of the feeding roller and the cover roller.

12. The cover film sticking device according to claim 1, wherein the conveyor includes:
a rotary arm provided near the load is turnable about a rotary shaft, a front end of the rotary arm being provided with U-shaped claw sections, and
the basket is capable of being inserted and held between the claw sections.

13. The cover film sticking device according to claim 4, wherein the load tank is movable into and out of the cover film sticking device, and
wherein the basket sensor includes a first and a second basket sensor which are arranged inside the cover film sticking device in positions above where the load tank is located when in the cover film sticking device,
the positions of the first and second basket sensor being arranged along a line parallel to a moving direction of the load tank,
the first basket sensor being located on an inner side of the cover film sticking device with respect to the second basket sensor.

14. The cover film sticking device according to claim 13, wherein when a detecting signal is received from both the first basket sensor and the second basket sensor, the basket is determined to be larger than when the detecting signal is received only from the first basket sensor.

15. The cover film sticking device according to claim 1, wherein the basket accommodating section is located above the waiting position.

16. The cover film sticking device according to claim 15, wherein the conveyor includes an elevating table for moving the basket from the waiting position to the basket accommodating section.

17. The cover film sticking device according to claim 1, wherein the end-of-roll detecting sensor determines whether or not the amount of the cover film remaining on the film roll is sufficient to form the cover film piece to be pressed onto the next basket determined by sensing or not sensing a mark provided near a rear end of the film roll.

18. The cover film sticking device according to claim 1, further comprising:
a movable hook pusher which is adapted to turn down a hook on a top of the basket, so that the slide glasses stored in the basket are not interfered with by the hook when being are taken out of and restored to the basket.

* * * * *